(12) United States Patent
Tao

(10) Patent No.: US 9,237,852 B2
(45) Date of Patent: Jan. 19, 2016

(54) PROBE

(75) Inventor: Shoichi Tao, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 235 days.

(21) Appl. No.: 14/118,487

(22) PCT Filed: May 11, 2012

(86) PCT No.: PCT/JP2012/062115
§ 371 (c)(1),
(2), (4) Date: Nov. 18, 2013

(87) PCT Pub. No.: WO2012/157552
PCT Pub. Date: Nov. 22, 2012

(65) Prior Publication Data
US 2014/0114197 A1    Apr. 24, 2014

(30) Foreign Application Priority Data
May 18, 2011    (JP) .................................. 2011-111359

(51) Int. Cl.
*A61B 8/00* (2006.01)
*A61B 5/00* (2006.01)

(52) U.S. Cl.
CPC ............. *A61B 5/0071* (2013.01); *A61B 5/0084* (2013.01)

(58) Field of Classification Search
CPC ............................ A61B 5/0071; A61B 5/0084
USPC ........................................................... 600/478
See application file for complete search history.

(56) References Cited

FOREIGN PATENT DOCUMENTS

| JP | 56-158304 | 12/1981 |
|----|-----------|---------|
| JP | 60-205414 | 10/1985 |
| JP | 2010-88665 | 4/2010 |
| JP | 2010-088929 | 4/2010 |
| JP | 2010-104391 | 5/2010 |

*Primary Examiner* — Bo J Peng
(74) *Attorney, Agent, or Firm* — Cozen O'Connor

(57) ABSTRACT

A probe is shown. According to one implementation, the following is included at a tip of the probe, as the optical system. A first optical fiber system forms an irradiating light guiding path to guide irradiating light. A second optical fiber system forms a receiving light guiding path to guide measuring light. A condenser lens system is positioned opposed to the first optical fiber system and the second optical fiber system, and the irradiating light is irradiated thereon and the measuring light is condensed. An optical axis of the condenser lens system, a central axis of a light emitting end of the first optical fiber system, and a central axis of a light receiving end of the second optical fiber system are positioned so a straight line which passes through two axes does not pass through a remaining axis.

10 Claims, 15 Drawing Sheets $(D < 2d_1 + d_2)$ $(L < 2d_1 + d_2)$

PROBE

RELATED APPLICATIONS

This application is a U.S. National Phase Application under 35 USC 371 of International Application PCT/JP2012/062115 filed May 11, 2012.

This application claims the priority of Japanese application No. 2011-111359 filed May 18, 2011, the entire content of which is hereby incorporated by reference.

TECHNICAL FIELD

The present invention relates to a probe to measure the measuring light, the probe including an optical system to irradiate irradiating light on a measurement target site of live body tissue and to receive measuring light radiated from the measurement target site.

BACKGROUND ART

Observation and diagnosis of an internal lumen by an electronic endoscope is a diagnosis method widely used at present. Since this diagnosis method directly observes the internal tissue, there is an advantage that there is no need to cut a lesion portion, and the burden on a subject is small. On the other hand, such method which directly observes the internal lumen is considered to have lower certainty and accuracy compared to a pathological examination after a biopsy. Therefore, continuous effort is made to enhance quality of imaging.

Lately, other than a so-called videoscope, diagnosis devices which use various optical principles and ultrasonic diagnosis devices are proposed, and some are in practical use. In these areas, in order to improve the diagnosis certainty, new measuring principles are introduced, or a plurality of measuring principles are combined.

Specifically, it is known that information which cannot be obtained by simply looking at the image of the tissue can be obtained by observing and measuring fluorescence from the tissue and the fluorescence from the fluorescent material applied to the tissue. A fluorescent image endoscope system is proposed to obtain the fluorescent image, to overlap the fluorescent image to the normal visual image and to display the image. Such system is highly desired, because it is possible to discover a malignant tumor at an early stage.

Moreover, there is also known a method to judge a state of tissue by obtaining intensity information of fluorescence without configuring the fluorescent image. In such method, fluorescence is obtained without using the imaging element mounted in the electronic endoscope.

As a diagnosis tool for fluorescent diagnosis, in other words, probe, there are those which enter the body through a forceps channel of an endoscope, or those which are formed as one with the endoscope. The fluorescence observation probe described in Patent Document 1 and Patent Document 2 enter the body by inserting the probe in the forceps channel of the endoscope.

PRIOR ART DOCUMENT

Patent Document

Patent Document 1: Japanese Unexamined Patent Application Publication No. 2010-104391

Patent Document 2: Japanese Unexamined Patent Application Publication No. 2010-88929

DISCLOSURE OF THE INVENTION

Problems to be Solved by the Invention

However, the following problems can be seen in the conventional techniques.

As for the probe for observing fluorescence as described in Patent Document 1, although the probe includes an excitation light guiding path for guiding the excitation light, the probe does not include a receiving light guiding path for obtaining the fluorescence, and the fluorescence is received by a CCD of the endoscope to obtain the fluorescent image. Therefore, the fluorescence observing function cannot be completed by the probe alone. If the measuring light is received by the CCD of the endoscope as in the apparatus disclosed in Patent Document 1, the various pieces of information included in the measuring light cannot be fully used compared to methods such as a method in which light is dispersed to obtain signal intensity for each wavelength or a method in which only a specific wavelength region is extracted with an optical filter. Therefore, compared to guiding light with an optical fiber and detecting and processing in an external device, the flexibility in detecting the signal and processing the signal is low. This is a disadvantage for enhancing diagnosis accuracy.

As for the probe for observing fluorescence as described in Patent Document 2, both the excitation light and the fluorescence are guided by the same optical fiber, and the excitation light and the fluorescence are divided with the dichroic mirror provided in the base unit. When only the fluorescence is the target of measurement, such configuration is useful because of its simplicity. However, in order to enhance certainty of diagnosis, it is desirable that various measurements can be done by the same probe, and such configuration in which only the measurement of fluorescence is the target lacks versatility.

In order to perform various optical measurement, it is desired that the probe can be applied to both cases where the wavelengths of the excitation light and the measuring light are the same (elastic process), and where the energy of the excitation light and the measuring light are different (inelastic process). The probe for observing fluorescence as described in Patent Document 2 divides the excitation light and the fluorescence with the dichroic mirror, and therefore there is a problem that the excitation light and the measuring light cannot be divided when the wavelengths are the same or close.

The present invention has been conceived in view of the above problems, and it is an object of the present invention to provide an optical measurement probe which can be adapted to both the elastic process and the inelastic process. Specifically, considering a situation where various optical elements need to be provided in a small diameter to be inserted in the body, the object of the present invention is to provide an optical measurement probe which can sufficiently divide the irradiating light and the measuring light without using the dichroic lens and which includes an optical system provided in a small diameter.

Means for Solving the Problem

In order to solve the above problems, according to the invention of claim 1, there is provided a probe to measure measuring light including an optical system which irradiates irradiating light on a measurement target site of live body tissue and which receives measuring light radiated from the measurement target site, the probe including at a tip as the optical system:

a first optical fiber system which forms an irradiating light guiding path to guide the irradiating light;

a second optical fiber system which forms a receiving light guiding path to guide the measuring light; and a condenser lens system which is positioned opposed to a light emitting end of the first optical fiber system and a light receiving end of the second optical fiber system, and on which the irradiating light is irradiated and the measuring light is condensed, wherein the first and the second optical fiber system each include one optical fiber or a bundle of a plurality of optical fibers;

the condenser lens system includes one or a plurality of lenses; and an optical axis of the condenser lens system, a central axis of the light emitting end of the first optical fiber system, and a central axis of the light receiving end of the second optical fiber system are positioned under a condition that a straight line which passes through two among the three axes does not pass through a remaining one axis.

According to the invention of claim 2, the probe of claim 1, wherein, a diameter of a circumscribed circle of the first optical fiber system at the light emitting end of the first optical fiber system is to be $d_1$;

a diameter of a circumscribed circle of the second optical fiber system at a light receiving end of the second optical fiber system is to be $d_2$; and the light emitting end of the first optical fiber system and the light receiving end of the second optical fiber system are provided in a region where a diameter is smaller than diameter $2d_1+d_2$ with the optical axis of the condenser lens system as a central axis.

According to the invention of claim 3, the probe of claim 2, wherein a region a distance $d_2/2$ or more inward from an outer circumference of an inner region where the light emitting end of the first optical fiber system and the light receiving end of the second optical fiber system can be provided is to be a region α;

a region with a diameter smaller than a diameter $d_1+d_2$ including as a central axis the central axis of the light emitting end of the first optical fiber system is to be a region β;

a region with a diameter smaller than the diameter $d_1+d_2$ including as a central axis an axis in a position symmetrical to the central axis of the light emitting end of the first optical fiber system with the optical axis of the condenser lens system as a center is to be a region γ; and the central axis of the light receiving end of the second optical fiber system is positioned in a region within the region α not including the region β and the region γ.

According to the invention of claim 4, the probe of claim 2, wherein, a diameter including as a central axis the optical axis of the condenser lens system in an inner region where the light emitting end of the first optical fiber system and the light receiving end of the second optical fiber system can be provided is to be a probe effective internal diameter D ($D<2d_1+d_2$); and the first optical fiber system, the second optical fiber system, and the condenser lens system are positioned so that a distance $d_3$ between an axis in a position symmetrical to the central axis of the light emitting end of the first optical fiber system with the optical axis of the condenser lens system as a center and the central axis of the light receiving end of the second optical fiber system satisfies a relation of $(d_1+d_2)/2<d_3<D-(d_1+d_2)/2$.

According to the invention of claim 5, the probe of any one of claims 1 to 4, wherein, the first optical fiber system and the second optical fiber system are positioned so that at least a portion of an outer circumference comes into contact with each other.

According to the invention of claim 6, the probe of any one of claims 1 to 4, wherein, the first optical fiber system and the second optical fiber system are positioned separated from each other.

According to the invention of claim 7, the probe of claim 5 or 6, wherein, at least one of the first and the second optical fiber systems includes a bundle of a plurality of optical fibers, and a portion of an outer circumference of the other optical fiber system is positioned within a circumscribed circle of the one optical fiber system including the bundle of plurality of optical fibers.

According to the invention of claim 8, the probe of claim 5 or 6, wherein, at least one of the first and the second optical fiber systems includes a bundle of a plurality of optical fibers, and an outer circumference of the other optical fiber system is not positioned within a circumscribed circle of the one optical fiber system including the bundle of plurality of optical fibers.

According to the invention of claim 9, the probe of any one of claims 3 to 8, wherein, a distance described below is a range from a same size to 1.4 times a focal length of the condenser lens, the distance between (i) the light emitting end of the first optical fiber system and the light receiving end of the second optical fiber system and (ii) a first surface of a lens which is included in the condenser lens system and which is closest to a second optical fiber system side, the first surface on a light receiving end side of the second optical fiber system.

According to the invention of claim 10, the probe of any one of claims 3 to 9, wherein, a ratio $r_1/r_2$ is within a range of −0.05 to 0.05 when a curvature radius of a first surface of the condenser lens is $r_1$ and a curvature radius of a second surface opposite of the first surface is $r_2$.

Advantageous Effect of the Invention

The reflecting light from the condenser lens system concentrates in a position symmetrical to the central axis of the light emitting end of the first optical fiber system with the optical axis of the condenser lens system as the center. According to the present invention, the optical axis of the condenser lens system, the central axis of the light emitting end of the first optical fiber system, and the central axis of the light receiving end of the second optical fiber system are positioned under the condition that assuming a straight line which two of the three axes pass through, the remaining one axis does not pass through the straight line. Therefore, compared to when the three axes pass through the same straight line, it is possible to position the optical systems in the small diameter. Moreover, since the central axis of the light receiving end of the second optical fiber system is separated from the symmetrical position, the reflecting light from the condenser lens system which enters the second optical fiber system can be reduced. In addition to satisfying the conditions of being able to position the optical systems in the small diameter and being able to reduce the reflecting light entering the second optical fiber system, it is possible to irradiate irradiating light guided by the first optical fiber system through the condenser lens system to the measurement target site of the live body tissue so that the measuring light radiated from the measurement target site can be condensed by the condenser lens system to enter the second optical fiber system. Therefore, in both the elastic process and the inelastic process, the irradiating light and the measuring light can be divided, and the diameter of the probe can be made smaller.

EMBODIMENT FOR CARRYING OUT THE INVENTION

Figure 1:
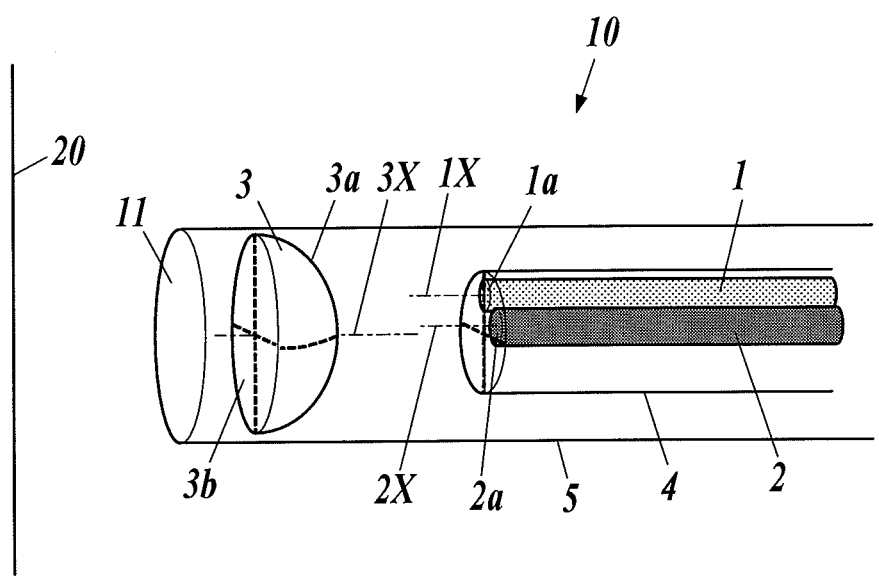
FIG. 1 is a schematic diagram of a tip end section of a probe according to an embodiment of the present invention.

An embodiment of the present invention is described with reference to the drawings. Below is merely one embodiment of the present invention and is not intended to limit the present invention.

A first optical fiber system 1, a second optical fiber system 2, and a condenser lens system are provided inside a probe 10 of the present embodiment. The first optical fiber system 1 composes the irradiating light guiding path which guides the irradiating light. The second optical fiber system 2 composes the receiving light guiding path which guides the measuring light.

The first and second optical fiber systems 1 and 2 are each one optical fiber or an optical fiber bundle including a bundle of a plurality of optical fibers and are held by a fiber holding member 4.

The condenser lens system is composed of one lens or a plurality of lenses. When the condenser lens system is composed of one lens, the lens is to be a condenser lens 3, and when the condenser lens system is composed of a plurality of lenses, the lens provided in a position closest to the optical fiber systems 1 and 2 is to be the condenser lens 3. A tip end of the first optical fiber system 1 opposite of the condenser lens 3 is a light emitting end 1a and a tip end of the second optical fiber system 2 opposite of the condenser lens 3 is a light receiving end 2a.

Regarding the surface of the condenser lens 3, the side opposite of the light emitting end 1a of the first optical fiber system 1 and the light receiving end 2a of the second optical fiber system 2 is to be the first surface 3a, and the side opposite of the first surface 3a is to be the second surface 3b. The condenser lens 3 is a lens including positive power to achieve the function of condensing excitation light which is emitted to expand from the first optical fiber system 1 to the measurement target, and having the function of condensing the measuring light generated to expand from the measurement target to the periphery of the second optical fiber system 2. Typically, a lens in which the first surface 3a is a convex surface and the second surface 3b is a substantial planar surface is used as the condenser lens 3.

The light emitting end 1a of the first optical fiber system 1, the light receiving end 2a of the second optical fiber system 2, and the condenser lens 3 are maintained in a relative position. Therefore, according to the present embodiment, the optical fiber systems 1 and 2 are fixed with a fiber holding member 4, and the condenser lens 3 and the fiber holding member 4 are fixed with a probe casing 5.

A window is provided on a tip end surface 11 of a probe 10 for transmitting and receiving light. The probe 10 is sealed to prevent liquid, etc. from flowing inside, and is a commonly called water tight configuration.

A base end of the probe 10 is connected to a base unit not shown. The base unit includes a light source of the excitation light, a spectroscope or a photodetector, an analyzer and the like. The base end of the first optical fiber system 1 is connected to the light source and the base end of the second optical fiber system 2 is connected to the spectroscope or the photodetector.

The excitation light from the light source is guided to the tip end section of the probe 10 with the first optical fiber system 1. The excitation light which is emitted from the light emitting end 1a of the first optical fiber system 1 is condensed with the condenser lens 3 and is emitted from the tip end surface 11 of the probe 10. Then, the light is irradiated on the measurement target site of a live body tissue surface 20. Fluorescence is generated by the excitation light irradiated on the measurement target site depending on the lesion state. The measuring light from the measurement target site including the generated fluorescence and the light reflected from the live body tissue surface 20 enters the probe 10 from the tip end surface 11, is condensed with the condenser lens 3, and enters the light receiving end 2a of the second optical fiber system 2. The measuring light is further guided with the second optical fiber system 2.

The measuring light guided by the second optical fiber system 2 is input to the spectroscope or the photodetector of the base unit. When X-rays, ultraviolet rays, and visible rays are irradiated on matter, the energy of the rays are absorbed and the electrons are excited. When this returns to a ground state, excess energy is released as electromagnetic rays. This is the fluorescence in a broad meaning. Here, due to the excitation light (reference light), the fluorescence with a wavelength different from the excitation light occurs as the returning light. The returning light is detected, the light is guided to the spectrometer of the base unit through the second optical fiber system 2, and the analysis of spectral distribution is performed. With this, the lesion state of the measurement target is detected.

The form of inserting the probe 10 into the body may be through a channel formed in the endoscope or may be a form of inserting the probe into the body alone independent from the endoscope. The probe 10 may be a form inserted into the body together with the endoscope by including the probe 10 in the endoscope.

The purpose of the probe 10 is to observe and diagnose the live body tissue with optical measurement. Other than the above described fluorescent measurement, the optical measurement specifically includes reflecting light measurement, but the optical measurement is not limited to the above.

FIG. 1 shows an optical axis 3X of the condenser lens 3, a central axis 1X of a light emitting end 1a of the first optical fiber system 1, and a central axis 2X of a light receiving end 2a of the second optical fiber system 2. The light emitting end 1a surface of the first optical fiber system 1 and the light receiving end 2a surface of the second optical fiber system 2 exist on substantially the same plane. The above optical systems 1, 2 and 3 are positioned to satisfy the conditions described below in order to be positioned in the small diameter of the tip end section of the probe 10 while reducing the reflecting light from the condenser lens 3 entering in the second optical fiber system 2 so that the measuring light from the live body tissue surface 20 enters the second optical fiber system 2 with high efficiency.

First, as the basic condition, the three axes 1X, 2X and 3X are positioned in a condition so that a straight line which passes through two of the axes does not pass the remaining one axis. The reflecting light from the condenser lens system 3 concentrates in a position symmetrical to the central axis 1X of the light emitting end of the first optical fiber system 1 with the optical axis 3X of the condenser lens system 3 as the center. By positioning the three axes 1X, 2X and 3X in a condition so that the straight line which passes through two of the three axes does not pass through the remaining one axis, it is possible to position the optical systems in the small diameter compared to when the three axes exist on the same straight line. Moreover, since the central axis 2X of the light receiving end of the second optical fiber system 2 is separated from the above described symmetrical position, the reflecting light from the condenser lens system 3 entering the second optical fiber system 2 can be reduced. Therefore, in both the elastic process and the inelastic process, the irradiating light and the measuring light can be sufficiently divided.

Here, the first optical fiber system 1 and the second optical fiber system 2 can be positioned so that at least a portion of each outer circumference comes into contact with each other or the first optical fiber system 1 and the second optical fiber system 2 can be positioned to be separated from each other. The former case is advantageous for making the diameter of the probe smaller and enhancing efficiency of receiving light. Moreover, in either the former case or the latter case (1) when at least one of the first and second optical fiber systems is composed of a bundle of plurality of optical fibers, a portion of the outer circumference of the other optical fiber system can be positioned to be within the circumscribed circle of the one optical fiber system composed of a bundle of a plurality of optical fibers, (2) the outer circumference of the other optical fiber system can be positioned so as not to be within the circumscribed circle of the one optical fiber system composed of a bundle of a plurality of optical fibers. The above case (1) is advantageous for making the diameter of the probe smaller and enhancing efficiency of receiving light. The above case (2) is easy to design because the optical fiber bundle can be handled approximately at the circumscribed circle.

According to the present embodiment, the condenser lens system and the two optical fiber systems are positioned according to the following conditions. As shown in FIG. 2, a plane coordinate on a plane perpendicular to the three axes 1X, 2X, 3X is assumed. The coordinate where the optical axis 3X of the condenser lens 3 is positioned is to be the point of origin O. The central axis 1X of the first optical fiber system 1 is positioned in the coordinate P1. When an axis in a position symmetrical to the central axis 1X of the first optical fiber system 1 with the optical axis 3X of the condenser lens 3 as the center is assumed, the axis is positioned in the coordinate <–P1>.

The diameter of the circumscribed circle of the first optical fiber system 1 in the light emitting end of the first optical fiber system 1 is to be $d_1$. When the first optical fiber system 1 is composed of one optical fiber, the diameter $d_1$ is equal to the outer circumference of the optical fiber, and when the first optical fiber system 1 is a bundle of optical fibers, the diameter $d_1$ is equal to the diameter of the circle circumscribed to the optical fiber in the far outer circumference. Similarly, the diameter of the circumscribed circle of the second optical fiber system 2 in the light receiving end of the second optical fiber system 2 is defined as $d_2$.

According to the present embodiment, in order to compose the tip end section of the probe 10 with a small diameter, the light emitting end 1a of the first optical fiber system 1 and the light receiving end 2a of the second optical fiber system 2 are provided in a region less than the diameter $2d_1+d_2$ with the optical axis 3X as the central axis. In other words, when the probe effective inner diameter D is to be the diameter of the inner region ω where the light emitting end 1a of the first optical fiber system 1 and the light receiving end 2a of the second optical fiber system 2 can be provided with the optical axis (point of origin O in FIG. 2A) as the central axis, the probe 10 is configured to satisfy the condition of $D<2d_1+d_2$. In FIG. 1, the inner diameter of the fiber holding member 4 is equal to D. Here, $2d_1+d_2$ is the amount corresponding to the minimum value of the effective inner diameter of the probe when the second optical fiber system 2 is positioned so as not to receive influence of the reflecting light from the condenser lens system 3 in a case where the axes in a position symmetrical to the central axis 1X of the first optical fiber system 1 with X1, X2 and the optical axis 3X of the condenser lens 3 as the center exist on one straight line. According to the present embodiment, the condition is $D<2d_1+d_2$, and the effective inner diameter of the probe is made even smaller than the above amount. Since it is necessary to store the first and second optical fiber systems in the holding member of the probe, the condition is $D \geq d_1+d_2$.

According to probe 10 of the present embodiment, the purpose of the above described configuration of the optical measurement probe 10 is to increase light receiving efficiency of the measuring light in both the elastic process and the inelastic process, and to decrease the light receiving amount of stray light other than the measuring light (for example, reflecting light from the lens surface, fluorescence from the lens and the like). The above purpose is achieved by the position of the condenser lens 3 and the optical fiber systems 1 and 2.

The first surface 3a of the condenser lens 3 has a convex surface shape, and the second surface 3b has a substantial planar surface shape. Here, the reflecting light from the first surface 3a spreads towards the first and second optical fiber systems 1 and 2. The reflecting light from the second surface 3b converges towards the first and second optical fiber systems 1 and 2. The light transmitted while spreading has a small power density and therefore hardly contributes as the stray light. In order to prevent receiving the reflecting light from the condenser lens 3, it is necessary to not receive light reflected on the second surface 3b and transmitted in the second optical fiber system 2 direction while condensing.

The main reflecting light from the condenser lens 3 can be kept off of the light receiving end 2a of the second optical fiber system 2 by the relative position between the condenser lens 3 and the optical fiber systems 1 and 2. In order to implement the above, the present embodiment uses the point that the condensing position of the reflecting light from the second surface 3b can be changed by not placing the first optical fiber system 1 on the optical axis 3X.

Figure 3:
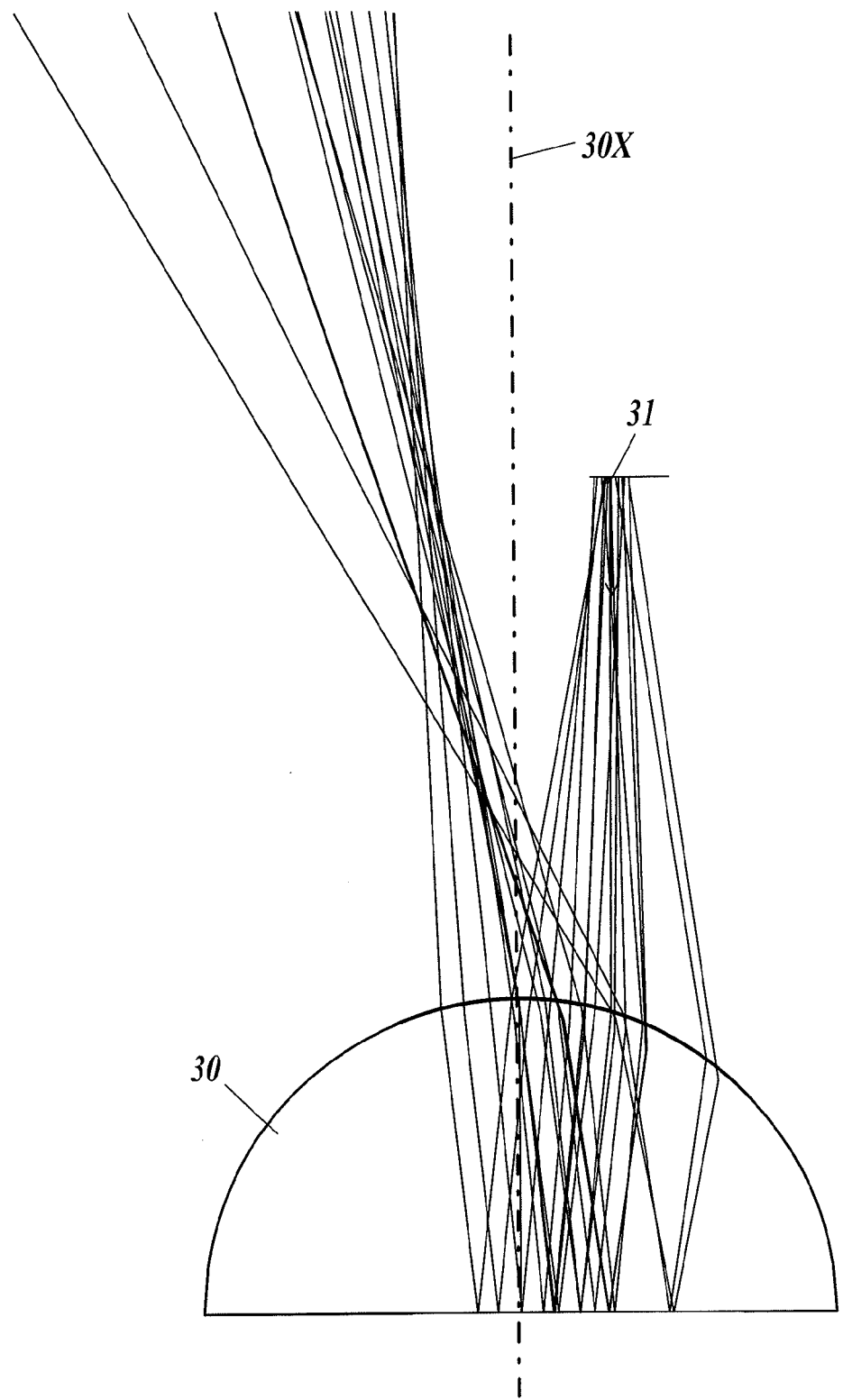
FIG. 3 is a diagram showing an optical path of light which enters a planar convex lens from a convex surface to be reflected with the planar surface.

The above is described using an example shown in FIG. 3. FIG. 3 shows a planar-convex lens 30. Light is emitted from the light emitting opening 31, which is in a position not aligned with the optical axis 30X of the planar-convex lens 30, towards the convex surface of the planar-convex lens 30. The light is reflected on the lens planar surface opposite of the convex surface. The ray of the emitting light and the reflecting light from the lens planar surface is shown in FIG. 3. Here, the refractive index of the lens 30 is $n_d=1.51633$, $v_d=64.1$, the curvature radius of the convex surface is 0.83 mm, the diameter of the planar surface is 1.66 mm, the distance between the lens planar surface and the light emitting opening 31 is 2.2 mm, the distance between the light emitting opening 31 and the lens optical axis 30X is 0.25 mm, the size of the light emitting opening 31 is $\phi 0.2$ mm, the NA of the emitting light is 0.22, and the wavelength is 632.8 nm.

As shown in FIG. 3, when the light emitting opening 31 is not aligned with the optical axis 30X, the condensing position of the reflecting light also becomes a position which is not aligned with the optical axis 30X.

As shown in FIG. 3, the reflecting light from the lens planar surface is condensed in a position misaligned in the direction opposite of the light emitting opening 31 in relation to the optical axis 30X. Specifically, the condensing position of the reflecting light from the second surface 3b of the condenser lens 3 is the position symmetrical to the central axis 1 of the first optical fiber system 1 with relation to the optical axis 3X. In other words, the substantial center of the condensed reflecting light from the condenser lens 3 is the coordinate <-P1> shown in FIG. 2. Moreover, the optical path length from the light emitting end 1a to the second surface 3b and the optical path length from the second surface 3b to the planar surface including the light receiving end 2a are substantially equal, and the second surface 3b is a substantial planar surface. Therefore, the diameter of the condensing spot of the reflecting light on the planar surface including the light receiving end 2a of the second optical fiber system 2 is similar to the diameter $d_1$ of the first optical fiber system 1.

In view of the above, the configuration condition of the probe is defined as follows.
(Configuration Condition 1)

As shown in FIG. 2, region $\alpha$ is the region separated a distance of $d_2/2$ or more inward from the outer circumference of the inner region $\omega$ where the light emitting end of the first optical fiber system 1 and the light receiving end of the second optical fiber system 2 can be provided.

The region $\beta$ is the region with a diameter less than $d_1+d_2$ with the central axis (P1 in FIG. 2) of the light emitting end of the first optical fiber system 1 as the central axis.

The region $\gamma$ is the region with a diameter less than $d_1+d_2$ in which the central axis is an axis (<-P1> in FIG. 2) in the position symmetrical to the central axis (P1 in FIG. 2) of the light emitting end of the first optical fiber system 1 with the optical axis (point of origin O in FIG. 2) as the center. In other words, the region $\gamma$ is the point symmetrical image of the region $\beta$ with relation to the optical axis.

Here, the central axis 2X of the light receiving end of the second optical fiber system 2 is positioned in the region $\delta$ which is the region within the region $\alpha$ not including the region $\beta$ and the region $\gamma$ (hatched portion in FIG. 2). With this, it is possible to position the light receiving end of the second optical fiber system 2 which is the optical fiber for receiving light in the position where the reflecting light from the condenser lens 3 is not substantially irradiated. Therefore, it is possible to receive the measuring light at a high efficiency, and it is possible to reduce the receiving amount of reflecting light from the lens surface. Moreover, influence of the reflecting light is not received so much regardless of whether the process is the elastic process or the inelastic process. Therefore, the problem of the optical filter provided to cut the reflecting light being effective in the inelastic process but not effective in the elastic process can be overcome, and the configuration can be applied to both the elastic process and the inelastic process.

Figure 2A:
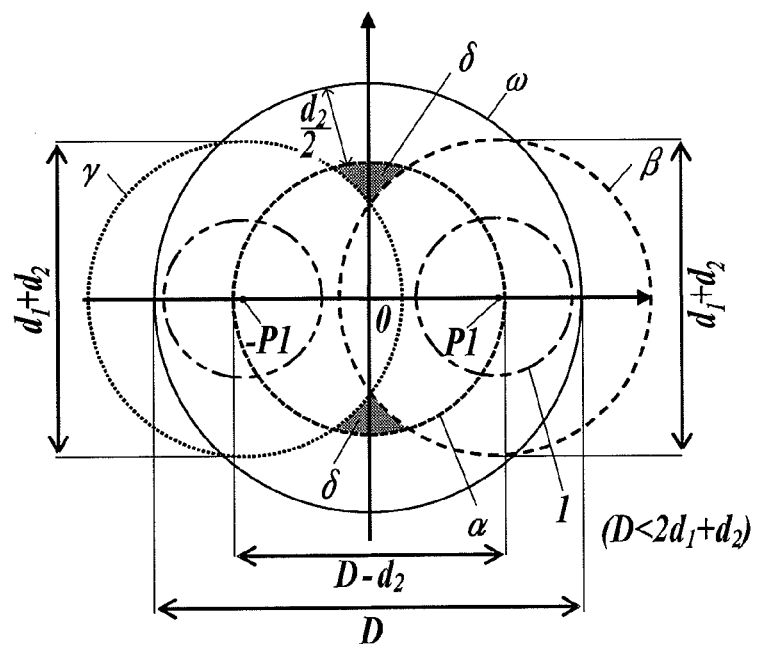
FIG. 2A is a drawing on a plane coordinate corresponding to a transverse cross section of the probe to show a configuration condition of the probe of the embodiment of the present invention.
Figure 2B:
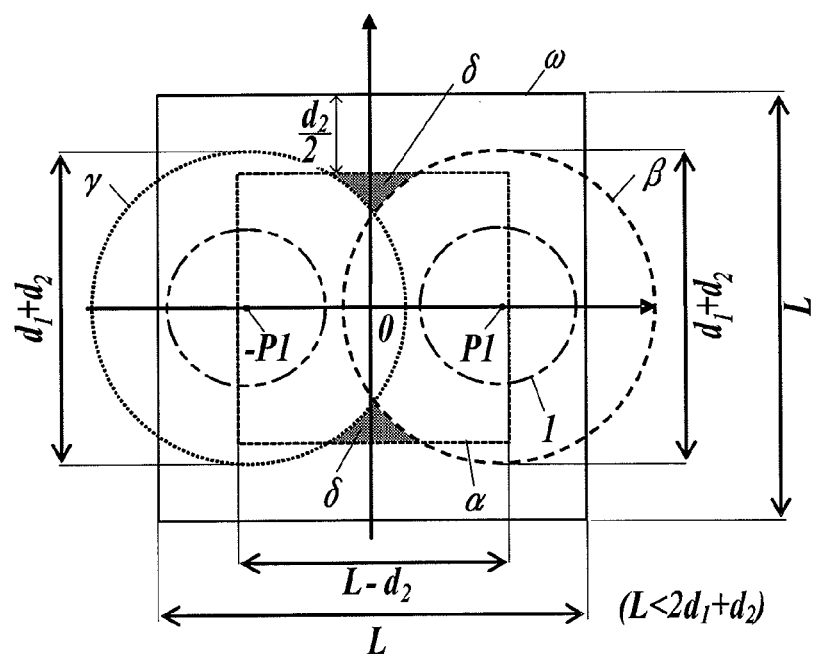
FIG. 2B is a drawing on a plane coordinate corresponding to a transverse cross section of the probe to show a configuration condition of the probe of the embodiment of the present invention.

Regarding the inner region $\omega$ and the region $\alpha$, the shape is not limited to a circular shape as shown in FIG. 2A, and the shape includes a polygonal shape such as a quadrangle as shown in FIG. 2B and other variants.

Here, it is preferable that the light emitting end of the first optical fiber system 1 and the light receiving end of the second optical fiber system 2 are positioned as close as possible to enhance efficiency of receiving the measuring light.

In order to achieve the above purposes, the configuration condition of the probe can be defined as the following.
(Configuration Condition 2)

The probe effective inner diameter D (note, $D<2d_1+d_2$) is the diameter of the inner region $\omega$ in which the light emitting end 1a of the first optical fiber system 1 and the light receiving end 2a of the second optical fiber system 2 can be provided with the optical axis (point of origin O) of the condenser lens system as the central axis.

The first optical fiber system, the second optical fiber system, and the condenser lens system are positioned to satisfy the relation $(d_1+d_2)/2 < d_3 < D-(d_1+d_2)/2$ where $d_3$ is the distance between the axis (−P1) in the position symmetrical to the central axis (P1) of the light emitting end $1a$ of the first optical fiber system 1 with the optical axis (point of origin O) of the condenser lens system as the center and the central axis 2X of the light receiving end of the second optical fiber system 2.

Among the conditional expression, "$(d_1+d_2)/2 < d_3$" represents the condition "not including the region γ" in the configuration condition 1 as an equation, and the purpose is to reduce the light receiving amount of the reflecting light from the lens surface.

Among the conditional expression, "$d_3 < D-(d_1+d_2)/2$" is included for the following reason.

Figure 4:
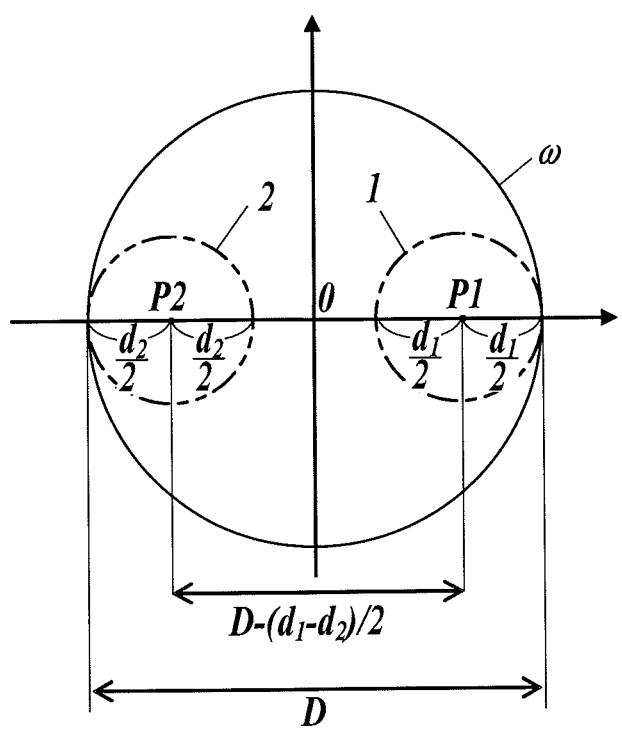
FIG. 4 is a drawing on a plane coordinate corresponding to a transverse cross section of the probe to describe a configuration condition of the probe of the embodiment of the present invention.

As shown in FIG. 4, a case is considered where the first optical fiber system 1 and the second optical fiber system 2 are positioned most separated in the inner region of the diameter D. Since the diameter of the first optical fiber system 1 is $d_1$ and the diameter of the second optical fiber system 2 is $d_2$, the distance between the center P1 of the first optical fiber system 1 and the center P2 of the second optical fiber system 2 is $D-(d_1+d_2)/2$.

Therefore, the distance $d_3$ does not become larger than $D-(d_1+d_2)/2$, and thus this is to be the upper limit.

By positioning the optical system of the optical measurement probe as described above, the light receiving amount of the lens reflecting light can be reduced and the light receiving amount of the measuring light from the measurement target can be secured. Further, by setting the curvature of the condenser lens 3 and the distance between the first and second optical fiber systems 1 and 2 and the condenser lens 3 to a predetermined value, it is possible to prevent the increase of the light receiving amount of the lens reflecting light due to error in positioning when providing both optical fiber systems 1 and 2 in the light emitting plane.

In order to realize the above, the distance from the light emitting end $1a$ of the first optical fiber system 1 and the light receiving end $2a$ of the second optical fiber system 2 to the opposing first surface $3a$ of the condenser lens 3 is set to a range from the same to 1.4 times as the focal length of the condenser lens 3. The ratio $r_1/r_2$ between the curvature radius $r_1$ of the first surface $3a$ of the condenser lens 3 and the curvature radius $r_2$ of the second surface $3b$ opposite of the first surface $3a$ is set to a range from −0.05 to 0.05.

EXAMPLES

Figure 5A:
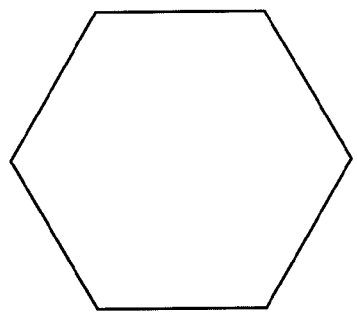
FIG. 5A is a diagram showing an example of a shape of a transverse cross section of a probe.
Figure 5B:
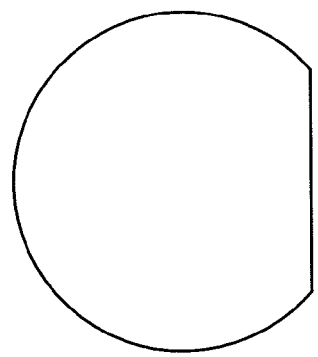
FIG. 5B is a diagram showing an example of a shape of a transverse cross section of a probe.
Figure 5C:
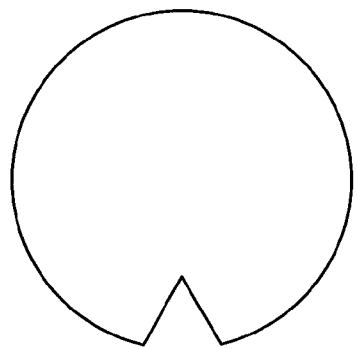
FIG. 5C is a diagram showing an example of a shape of a transverse cross section of a probe.

The examples below show that, according to the configuration conditions 1 and 2, the second optical fiber system 2 is able to avoid the reflecting light from the condenser lens 3, and the second optical fiber system 2 is able to effectively receive the measuring light from the measurement target even if the effective inner diameter of the probe is small. The specific numeric value shown below is a value set for the purpose of description, and does not limit the configuration of the present invention. The examples below assume a case when the probe is a cylinder shape, however, the probe may have a cross sectional shape which is a polygon (FIG. 5A), a D-shape (FIG. 5B) or a circle (FIG. 5C) or polygon with a cut out portion.

Figure 6:
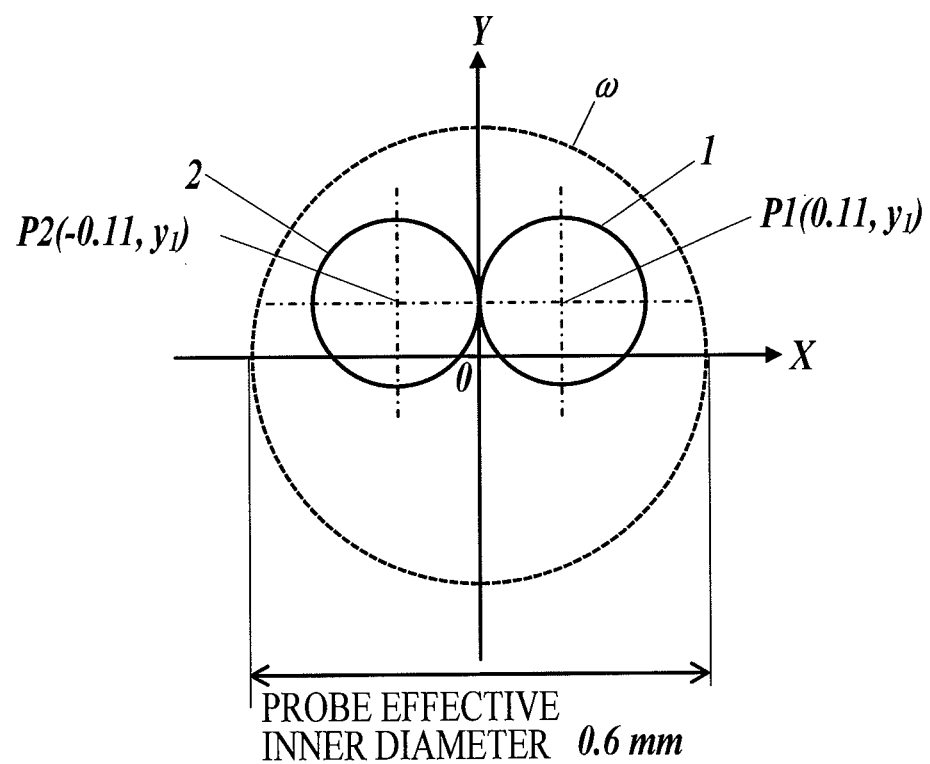
FIG. 6 is a drawing on a plane coordinate corresponding to a transverse cross section of the probe according to example 1 of the present invention.

The example 1 includes the following configuration conditions. The cross sectional view of the example 1 is shown in FIG. 6.

$d_1$=0.22 mm
$d_2$=0.22 mm
D=0.6 mm
P1=(0.11, $y_1$)
refraction index of nitride of condenser lens 3 $n_d$=1.51633, $v_d$=64.1
curvature radius of first surface of condenser lens 3 $r_1$=0.83 mm, second surface $3b$ is planar surface
distance between condenser lens 3 and light emitting end of first optical fiber system 1, 1.57 mm FIG. 7 shows a result of research by simulating the change of the light receiving efficiency and the lens reflecting light amount when $y_1$ is changed under the above configuration conditions. The light receiving efficiency is shown by the light receiving amount of the second optical fiber with respect to the optical amount of the emitting light from the first optical fiber.

Figure 7A:
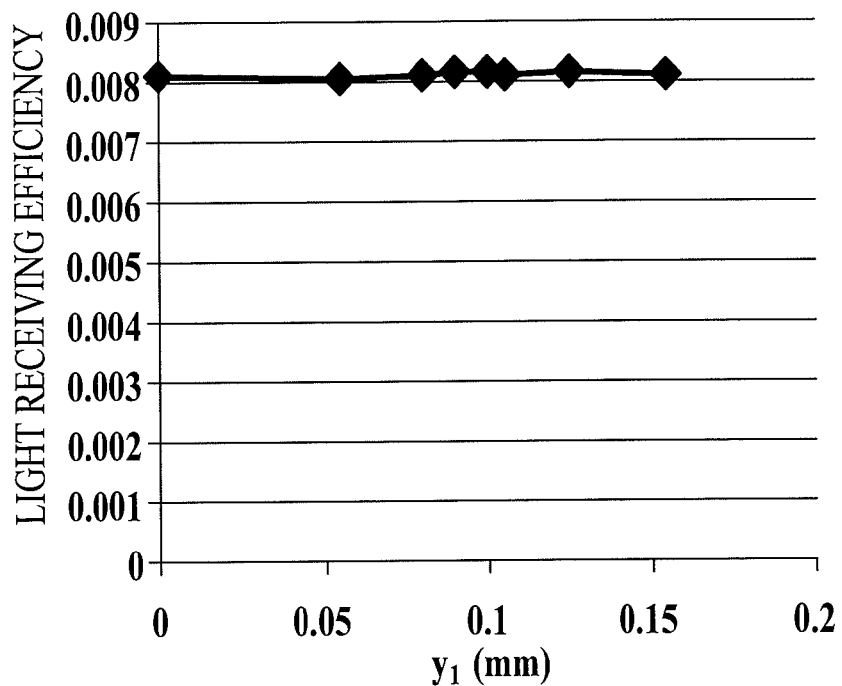
FIG. 7A is a graph showing a simulation result regarding example 1 of the present invention.
Figure 7B:
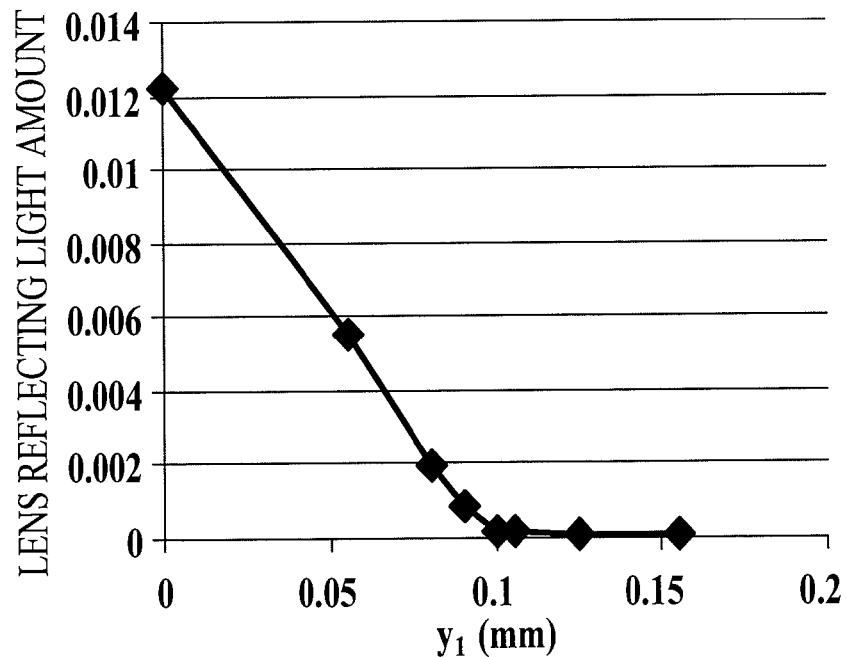
FIG. 7B is a graph showing a simulation result regarding example 1 of the present invention.
Figure 8A:
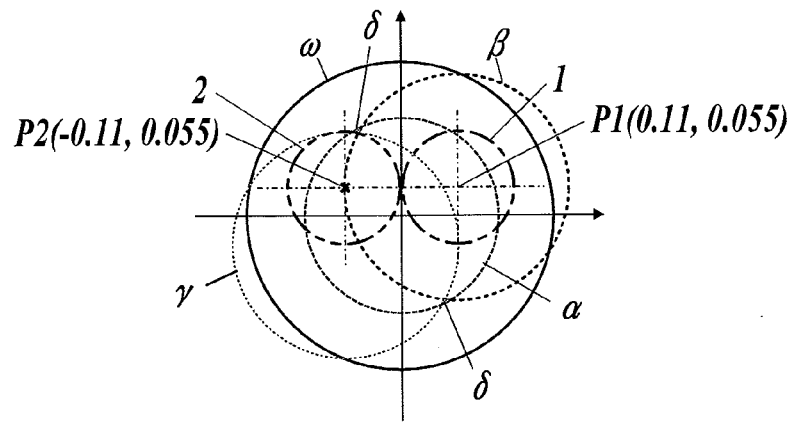
FIG. 8A is a drawing on a plane coordinate corresponding to a transverse cross section of the probe to show a configuration condition of example 1 of the present invention.
Figure 8B:
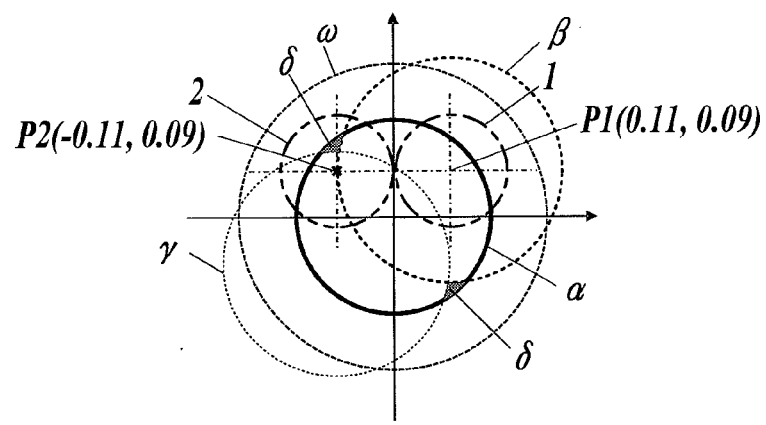
FIG. 8B is a drawing on a plane coordinate corresponding to a transverse cross section of the probe to show a configuration condition of example 1 of the present invention.
Figure 8C:
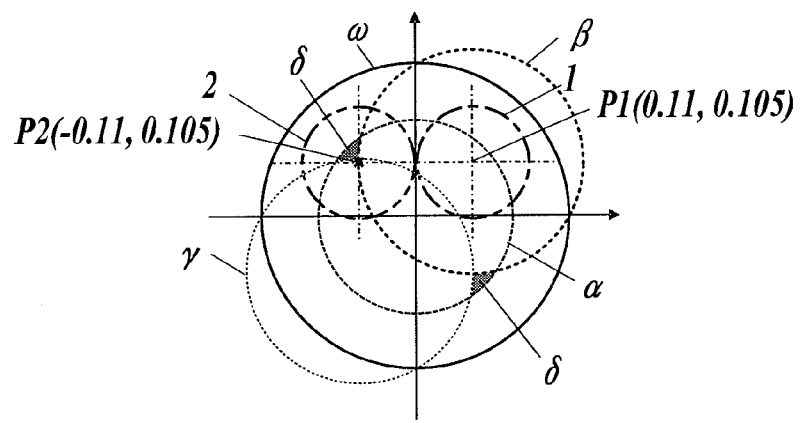
FIG. 8C is a drawing on a plane coordinate corresponding to a transverse cross section of the probe to show a configuration condition of example 1 of the present invention.
Figure 8D:
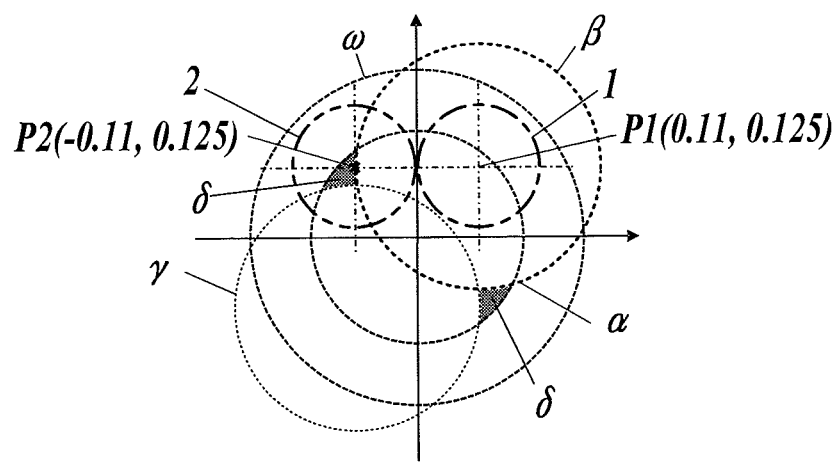
FIG. 8D is a drawing on a plane coordinate corresponding to a transverse cross section of the probe to show a configuration condition of example 1 of the present invention.
Figure 8E:
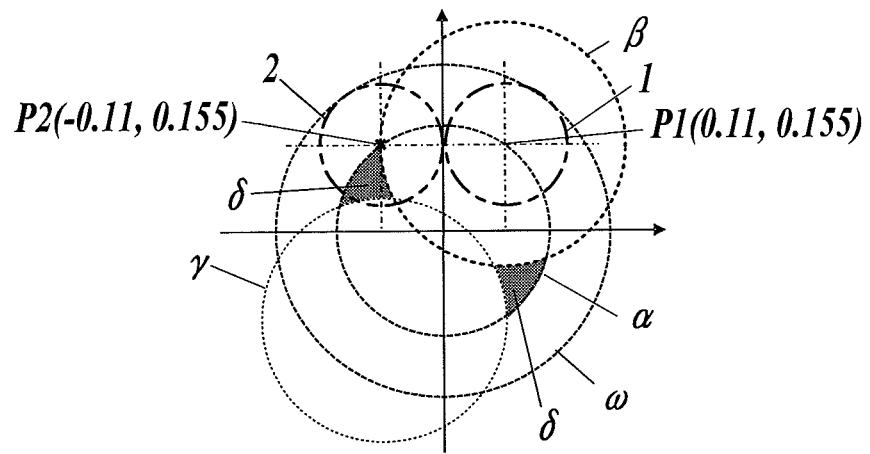
FIG. 8E is a drawing on a plane coordinate corresponding to a transverse cross section of the probe to show a configuration condition of example 1 of the present invention.

As shown in FIG. 7A, the light receiving efficiency is substantially a certain amount regardless of $y_1$. However, as shown in FIG. 7B, the lens reflecting light amount reduces as $y_1$ increases, and the lens reflecting light amount becomes almost 0 when $y_1$ is almost 0.1 or more. When $y_1$ is 0.1, the center P2 of the second optical fiber system 2 is (−0.11, 0.1), and the center of the region γ of the configuration condition 1 is (−0.11, −0.1). Therefore, the distance between the two is 0.2, and this almost matches with the lower limit value of the configuration condition 2 $(d_1+d_2)/2$=0.22.

FIG. 8 shows a position relation based on the configuration condition 1. The numeric value is changed to be $y_1$=0.055 in FIG. 8A, $y_1$=0.09 in FIG. 8B, $y_1$=0.105 in FIG. 8C, $y_1$=0.125 in FIG. 8D, and $y_1$=0.155 in FIG. 8E. With this, when $y_1$>0.1 where the lens reflecting light amount reduces, the center P2 of the second optical fiber system 2 is confirmed to be within the region δ of the configuration condition 1.

The example 2 includes the following configuration conditions. The cross sectional view of the example 2 is shown in FIG. 9.

Figure 9:
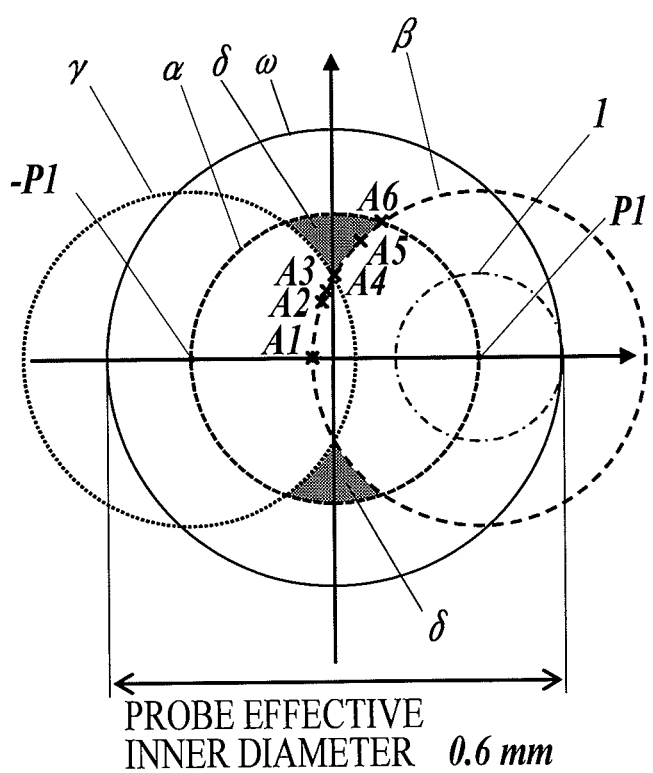
FIG. 9 is a drawing on a plane coordinate corresponding to a transverse cross section of the probe to show a configuration condition of the probe of example 2 of the present invention.

$d_1$=0.22 mm
$d_2$=0.22 mm
D=0.6 mm
P1=(0.19, 0)
−P1=(−0.19, 0)
refraction index of nitride of condenser lens 3 $n_d$=1.51633, $v_d$=64.1
curvature radius of first surface of condenser lens 3 $r_1$=0.83 mm, second surface $3b$ is planar surface distance between condenser lens 3 and light emitting end of first optical fiber system 1, 1.57 mm FIG. 10 shows a result of research by simulating the change of the light receiving efficiency and the lens reflecting light amount when the center P2 of the second fiber system 2 moves farther from the coordinate <−P1> corresponding to the center of the condensed reflecting light from the second surface $3b$ of the condenser lens 3 along the outer circumference in the region β as coordinates A1, A2, A3, A4, A5, A6 shown in FIG. 9 under the above configuration conditions. The horizontal axis in FIG. 10 shows the distance from the coordinate (−0.19, 0) of the center <−P1> of the region γ to the center P2 of the second optical fiber system 2.

Figure 10A:
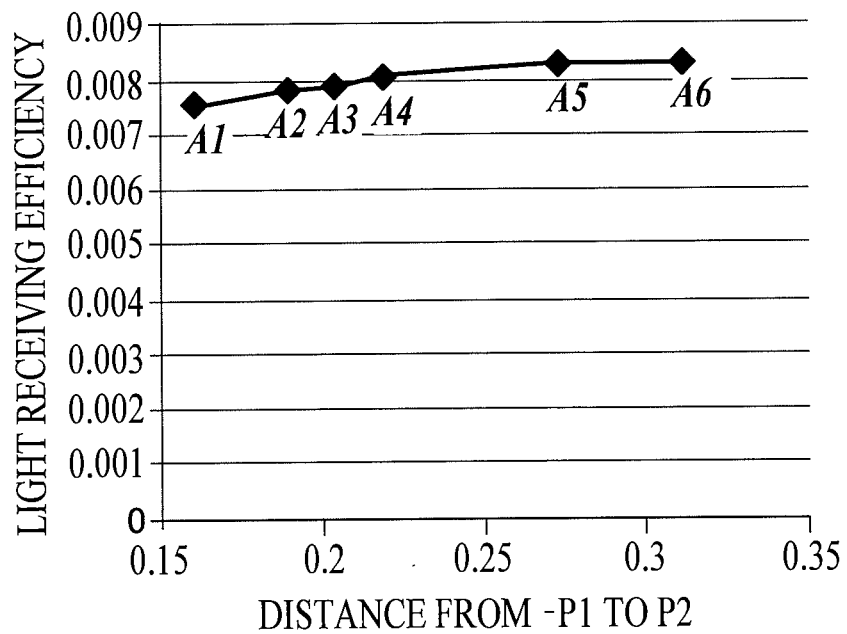
FIG. 10A is a graph showing a simulation result regarding example 2 of the present invention.
Figure 10B:
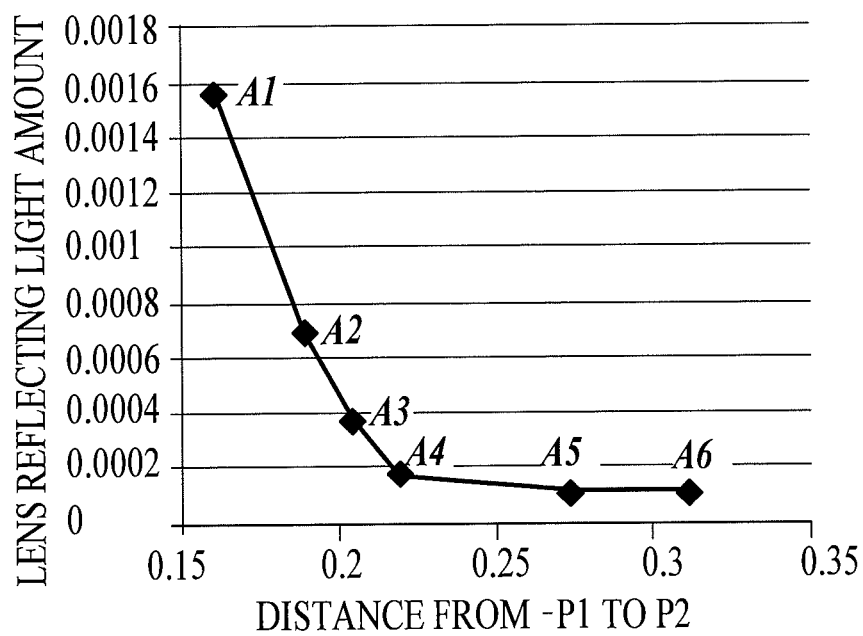
FIG. 10B is a graph showing a simulation result regarding example 2 of the present invention.

As shown in FIG. 10A, the light receiving efficiency is substantially a certain amount regardless of the distance, whereas as shown in FIG. 10B, the lens reflecting light amount greatly differs when the distance is about 0.22. Similar to example 1, this almost matches with the lower limit value of the configuration condition 2 $(d_1+d_2)/2$=0.22.

When, the center P2 of the second optical fiber system 2 is in the region δ shown in the configuration condition 1 (A4, A5, A6 of FIG. 7), it is confirmed that the lens reflecting light amount becomes small.

The example 3 includes the same configuration condition as the example 2.

Figure 11:
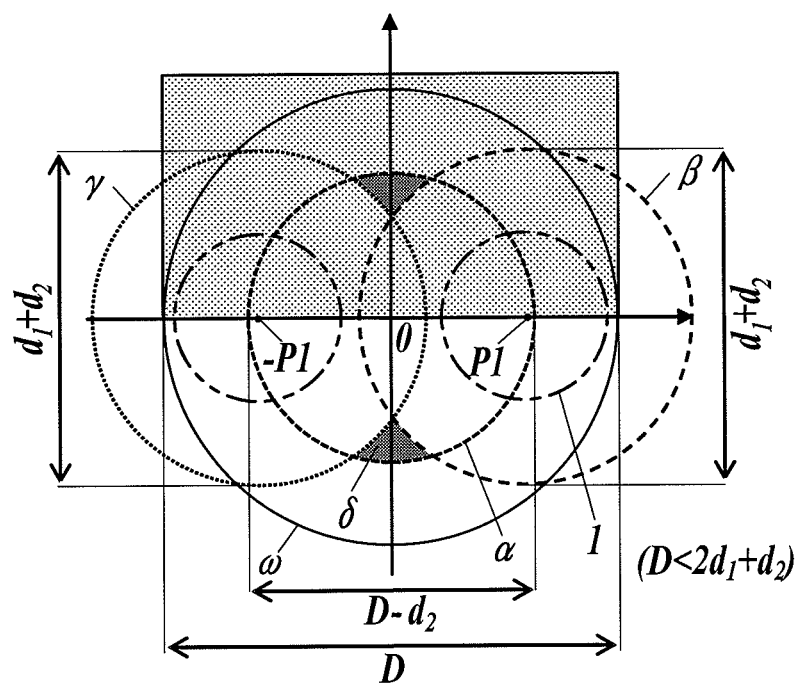
FIG. 11 is a drawing on a plane coordinate corresponding to a transverse cross section of the probe to show a configuration condition of example 3 of the present invention.
Figure 12:
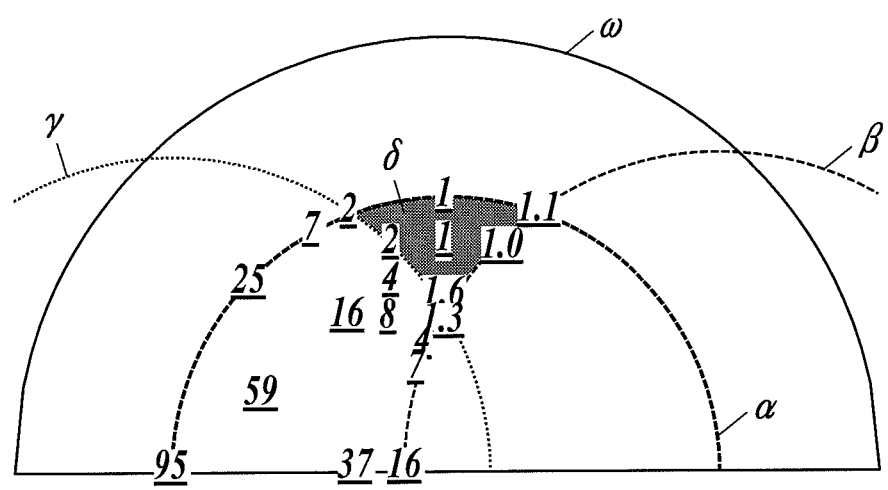
FIG. 12 is an enlarged diagram of a hatching region shown in FIG. 11.

In example 3, if a diagram drawing the border of the region according to the configuration condition 1 is drawn, the diagram becomes just like FIG. 11. An enlarged diagram of the hatching region of FIG. 11 is shown with FIG. 12. The numeric value displayed in FIG. 12 shows the lens reflecting light amount which the second optical fiber system 2 receives when the center P2 of the second optical fiber system 2 is provided in the position where the numeric value is displayed. For the purpose of ease of display, the numeric value displays 10000 times the actual number.

As shown in FIG. 12, the lens reflecting light amount is 4 or more in the region γ, whereas the lens reflecting light amount is 2 or less in the region δ. Therefore, it was found that the lens reflecting light becomes low throughout the entire region of the region δ shown with the configuration condition 1.

Described below is the reason why the lens reflecting light amount reduces under the configuration condition 1 or 2 as shown in the above described examples 1, 2 and 3.

Below, unless specifically noted, the description regarding the position of the optical fiber system includes the light emitting end 1a of the first optical fiber 1, and the planar surface perpendicular to the first optical fiber system 1 is to be the target. Moreover, the planar surface is called the light emitting planar surface.

Some of the light which is emitted from the first optical fiber system 1 is reflected on both surfaces of the condenser lens 3. First, for the ease of description, a planar-convex lens is described where the near surface from the view of the optical fiber systems 1 and 2 is the convex surface and the far surface is the planar surface. The light reflected on the convex surface advances towards the first and the second optical fiber systems 1 and 2 while spreading. Here, since the light is transmitted while spreading, the optical energy density is small. The light reflected on the planar surface transmits to be condensed around the first optical fiber system 1. When the optical axis is positioned to be not aligned with the center of the first optical fiber system 1, the reflecting light from the planar surface is also not aligned to almost the same degree in the direction opposite to the first optical fiber system 1 (position almost point symmetric to the optical axis). Therefore, the reflecting light from the condenser lens planar surface is distributed with the position of −P1 as the center on the light emitting planar surface. Moreover, the size of the distribution of the reflecting light from the condenser lens planar surface on the light emitting surface is considered to be equal to or larger than the size of the first optical fiber system 1 from consideration of geometric optics, and the minimum value of the diameter can be approximated to $d_1$. The above is the reason for drawing the border of the region γ.

The region α is the condition corresponding to positioning the second optical fiber system 2 separated in a distance equal to or larger than the radius of the second optical fiber system from the probe effective inner diameter D in order to position the second optical fiber system 2 within the probe effective inner diameter D, and is determined from only D and $d_2$.

The region β is the condition for positioning the second optical fiber system 2 around the first optical fiber system 1, corresponds to the necessity of providing P1 and P2 separated in the length of the radius of the optical fiber systems 1 and 2, and is determined from only $d_1$ and $d_2$.

In other words, from the geometric condition (outside region α and outside region β) to be able to provide the second optical fiber system 2, the configuration condition 1 is the region other than the region γ which condenses the reflecting light from the condenser lens 3.

As described above, only the region γ is derived from the optical conditions. As described as the configuration condition 2, the condition that the center of the second optical fiber system 2 is outside the region γ is represented as $(d_1+d_2)/2 < d_3$, using $d_3$ which is the distance between the coordinate <−P1> and the coordinate P2, and the diameters $d_1$ and $d_2$ of both optical fiber systems 1 and 2.

In addition to the above, it is preferable that the first and the second optical fiber systems 1 and 2 are positioned as close as possible so that the measuring light from the measurement target can be received effectively by the second optical fiber system 2.

The above is the description using the planar-convex lens, and the important point is the optical characteristic that "the reflecting light from the planar surface is not aligned in almost the same degree in the direction opposite to the first optical fiber system 1 (position almost point symmetric with respect to the optical axis)." According to this characteristic, the reflecting light from the condenser lens 3 can be distanced from the first optical fiber system 1 on the light emitting planar surface. Such characteristic can be seen when the curvature radius of the first surface 3a of the condenser lens 3 is larger than the curvature radius of the second surface 3b, the first surface 3a is the convex surface, and the second surface 3b is substantially the planar surface. When the lens is not the planar-convex lens, the distribution of the reflecting light from the second surface 3b of the condenser lens within the light emitting planar surface may become larger than the region γ, however by following the configuration condition 1 or 2, $(d_1+d_2)/2 < d_3$ is satisfied, and it is possible to reduce the light receiving amount of the lens reflecting light received by the second optical fiber system 2.

In the optical system of the optical measurement probe which is positioned as described above so that the light receiving amount of the lens reflecting light is reduced and the light receiving amount of the measuring light from the measurement target is secured, by further setting the curvature of the condenser lens 3 or the distance from the first and the second optical fiber systems 1 and 2 to the condenser lens 3 to a predetermined value, the increase of the lens reflecting light receiving amount due to the error in setting the position of the optical fiber systems 1 and 2 in the light emitting planar surface is prevented.

In order to achieve the above, the distance from the light emitting end 1a of the first optical fiber system 1 and the light receiving end 2a of the second optical fiber system 2 to the opposing first surface 3a of the condenser lens 3 is set to a range from 1 to 1.4 times the focal length of the condenser lens 3, and the ratio $r_1/r_2$ between the curvature radius $r_1$ of the first surface 3a of the condenser lens 3 and the curvature radius $r_2$ of the second surface 3b opposite of the first surface 3a is set to the range from −0.05 to 0.05.

Next, the setting distance of the condenser lens 3 with respect to the optical fiber systems 1 and 2 considering the positioning error and the setting of the curvature radius ratio $r_1/r_2$ of the condenser lens 3 are described.

As described above, by configuring the probe according to the configuration conditions 1 or 2, it is possible to realize a configuration so that the second optical fiber system 2 hardly receives the reflecting light from the condenser lens 3.

However, since the lens reflecting light receiving amount sensitively changes according to the setting position of the optical fiber systems 1 and 2, in the actual systems, it is necessary to sufficiently reduce the lens reflecting light receiving amount considering the positioning error.

The optical fiber systems 1 and 2 need to be positioned in the position according to the configuration conditions 1 and 2 even if the error is considered. As can be seen from the above examples 1, 2, and 3, the lens reflecting light receiving amount tends to increase near the border between the region γ. Therefore, the configuration to reduce the lens reflecting light receiving amount near the border is the configuration with high stability against positioning error of the optical fiber systems 1 and 2. As a way to realize such configuration, it is effective to finely adjust the curvature of the condenser lens 3 and to finely adjust the distance between the light emitting surface of the optical fiber system 1 and the condenser lens 3.

The effectiveness is described below based on example 4.

Figure 13:
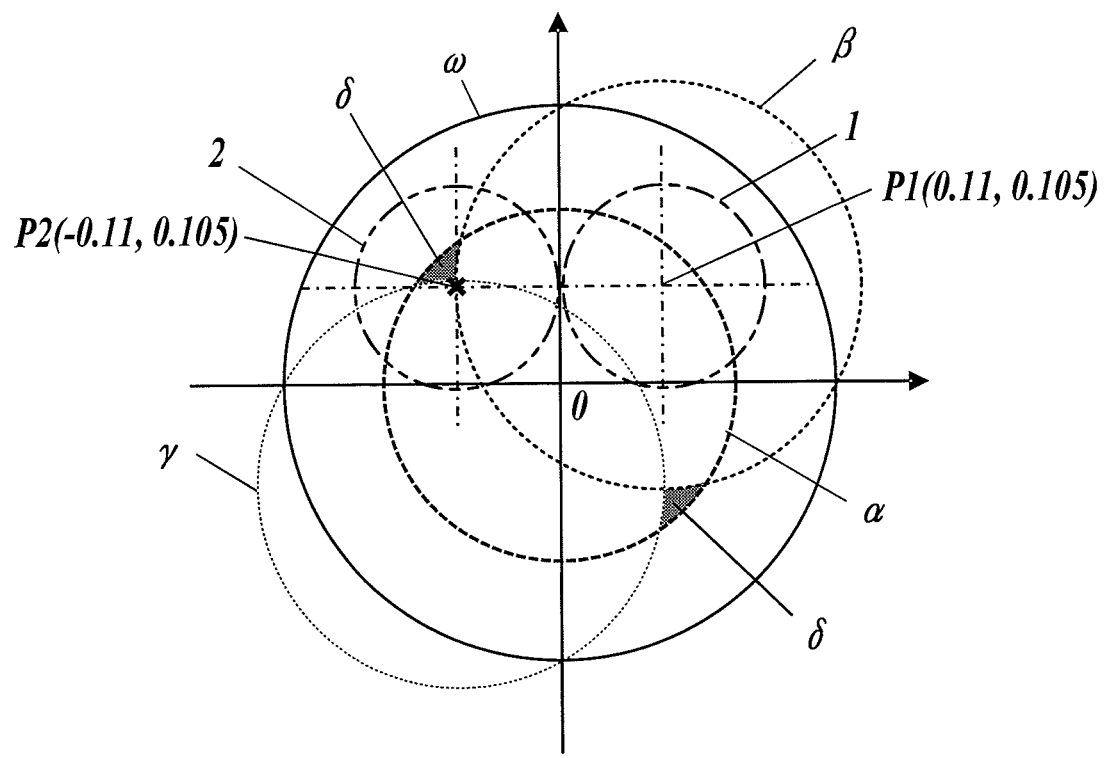
FIG. 13 is a drawing on a plane coordinate corresponding to a transverse cross section of the probe to show a configuration condition of example 4 of the present invention.

The example 4 includes the following configuration conditions. The cross sectional view of the example 4 is shown in FIG. 13.

$d_1$=0.22 mm
$d_2$=0.22 mm
D=0.6 mm
P1=(0.11, 0.105)
P2=(−0.11, 0.105)

refraction index of nitride of condenser lens 3 $n_d$=1.51633, $v_d$=64.1 curvature radius $r_1$ of first surface of condenser lens 3, curvature radius $r_2$ of second surface ($1/r_1+1/r_2=1/0.83$, and focal length in paraxial optics is not changed), $-0.05<r_1/r_2<0.05$ (positive and both convex)

distance between condenser lens 3 and light emitting end of first optical fiber system 1, 1.37 to 2.12 (mm)

As a result of following the above conditions, the center P2 of the second optical fiber system 2 is near the border of the region γ as shown in FIG. 13.

According to the above conditions, FIG. 14 is a graph showing the amount of the reflecting light, which is reflected on the condenser lens 3, received by the second optical fiber system 2 when the ratio $r_1/r_2$ and the distance between the condenser lens 3 and the light emitting end of the first optical fiber system 1 is changed. In the graph shown in FIG. 14, the distance between the condenser lens 3 and the light emitting end of the first optical fiber system 1 is shown by (distance from the focus position of the condenser lens 3 to the light emitting end of the first optical fiber system 1)/(focal length).

Figure 14A:
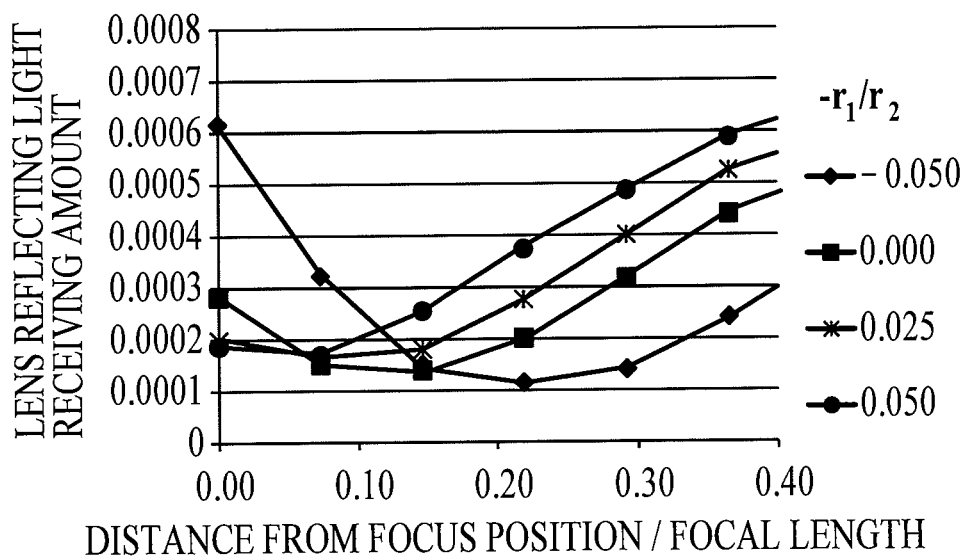
FIG. 14A is a graph showing a simulation result regarding example 4 of the present invention.

In the graph shown in FIG. 14A, the change of the lens reflecting light receiving amount with respect to the change of (distance from the focus position of the condenser lens 3 to the light emitting end of the first optical fiber system 1)/(focal length) is shown for each single lens when the focal length is not changed and the curvature radius is changed.

Referring to FIG. 14A, in a case where the lens is the planar-convex lens ($-r_1/r_2=0$), the lens reflecting light receiving amount becomes the minimum amount when the horizontal axis is about 0.15. Therefore, in a case where the lens is the planar-convex lens, it is possible to make the lens reflecting light receiving amount to a minimum value by setting the distance between the optical fiber system and the condenser lens to 1.15 times the focal length of the condenser lens. With this, it is possible to structure an optical system in which the optical performance hardly changes in response to error or change in the distance between the optical fiber system and the condenser lens. Moreover, it can be understood that the position of the minimum value shifts with the curvature of the lens.

Figure 14B:
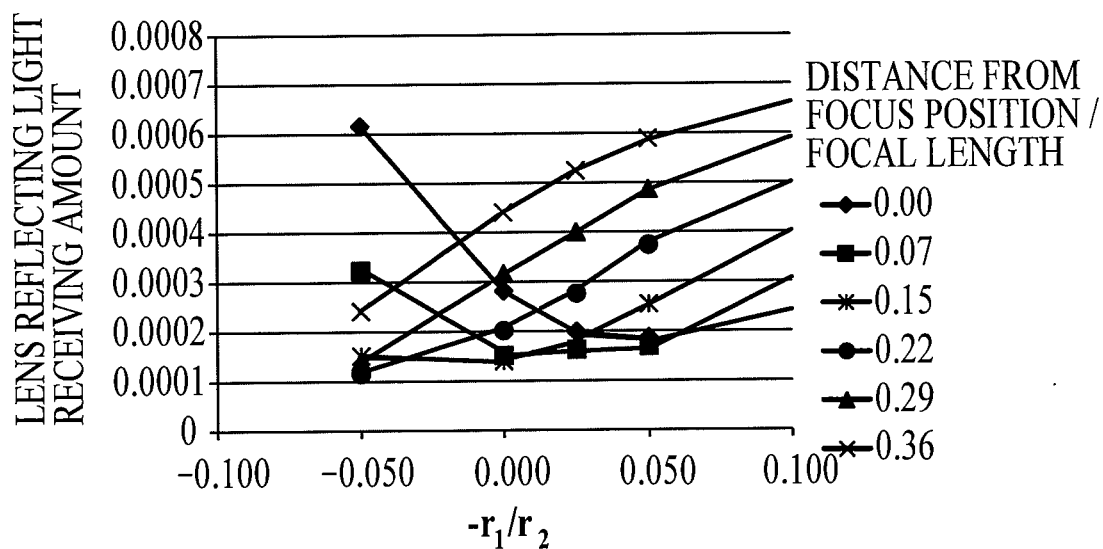
FIG. 14B is a graph showing a simulation result regarding example 4 of the present invention.

The similar effect can be achieved by adjusting the curvature radius of the lens. FIG. 14B is the graph showing the change of the lens reflecting light receiving amount with respect to the change of the curvature radius ratio "$-r_1/r_2$" for each configuration where the focal length is not changed and the distance from the focus position to the light emitting end of the fiber 1 is changed.

When the value of (distance from the focus position of the condenser lens 3 to the light emitting end of the first optical fiber system 1)/(focal length) is 0.15, the value is the minimum value when $-r_1/r_2$ is around 0.000. The curvature when the value is the minimum value changes according to the distance between the lens 3 and the fiber 1.

It is clear from FIG. 14A and FIG. 14B that the minimum value of the lens reflecting light amount can be achieved by adjusting the curvature radius ratio of the condenser lens and the distance between the optical fiber system 1 and the condenser lens 3. Therefore, when the position of the optical fiber 2 is near the border of the region defined by the above described configuration condition 1 and configuration condition 2, the lens reflecting light amount can be reduced by adjusting the curvature radius ratio of the condenser lens and the distance between the optical fiber system and the condenser lens. It can be seen from FIG. 14A and FIG. 14B that there is a position where the lens reflecting light receiving amount becomes the smallest by changing the distance between the optical fiber system 1 and the condenser lens 3 when the curvature radius ratio "$-r_1/r_2$" is at least between −0.05 and 0.05. Moreover, it can also be seen that the lens reflecting light receiving amount can be made smallest by changing the curvature of the condenser lens 3 when the distance between the optical fiber system 1 and the condenser lens 3 is at least 1.0 to 1.4 times the focal length of the condenser lens 3. In the present embodiment, the condenser lens system is configured from the single condenser lens. Alternatively, when the condenser lens system is configured from the plurality of lenses, the lens closest to the optical fiber system side is to be positioned to satisfy the above relation. The range shown here changes slightly depending on the refractive index of the nitrate material of the lens.

According to a configuration where the optical system is positioned so that the lens reflecting light receiving amount is smallest, not only is it possible to simply reduce the lens reflecting light receiving amount, but it is also possible to at least prevent increase of the lens reflecting light amount in response to the error with respect to the shape of the lens and the relative distance between the lens and the fiber.

It is clear from the above embodiments that when the light condenser lens and the optical fiber system are positioned, after the step of determining the position considering the configuration conditions 1 and 2, with the step to finely adjust the curvature radius ratio of the condenser lens and the distance between the optical fiber system and the condenser lens within the range acceptable under the specifications of the product, it is possible to create a probe in which the influence of the reflecting light from the condenser lens is sufficiently reduced.

According to the above embodiments, the optical fibers irradiate excitation light to the observation target site as well as receive the measuring light including the fluorescence generated by the excitation light. Alternatively, the scattering light or the Raman scattering light generated by the irradiating light can be received. In the above cases also, it is possible to diagnose the disorder state of the degeneration or cancer of the live body tissue, and the advantages of the present invention can be achieved.

INDUSTRIAL APPLICABILITY

The probe of the present invention can be used in the field of medicine where examination is performed by the endoscope.

DESCRIPTION OF REFERENCE NUMERALS 1 first optical fiber system
1a light emitting end
1X central axis
2 second optical fiber system
2a light receiving end
2X central axis
3 condenser lens
3a first surface (convex surface)
3b second surface (substantially planar surface)
3X optical axis
4 fiber holding member
5 probe casing
10 probe
11 tip end surface
20 live body tissue surface

The invention claimed is:

1. A probe to measure measuring light including an optical system which irradiates irradiating light on a measurement target site of live body tissue and which receives measuring light radiated from the measurement target site, the probe comprising at a tip as the optical system:
a first optical fiber system which forms an irradiating light guiding path to guide the irradiating light;
a second optical fiber system which forms a receiving light guiding path to guide the measuring light; and
a condenser lens system which is positioned opposed to a light emitting end of the first optical fiber system and a light receiving end of the second optical fiber system, and on which the irradiating light is irradiated and the measuring light is condensed,
wherein the first and the second optical fiber system each include one optical fiber or a bundle of a plurality of optical fibers;
the condenser lens system includes one or a plurality of lenses; and
an optical axis of the condenser lens system, a central axis of the light emitting end of the first optical fiber system, and a central axis of the light receiving end of the second optical fiber system are positioned under a condition that a straight line which passes through two among the three axes does not pass through a remaining one axis.

2. The probe of claim 1, wherein,
a diameter of a circumscribed circle of the first optical fiber system at the light emitting end of the first optical fiber system is to be $d_1$;
a diameter of a circumscribed circle of the second optical fiber system at a light receiving end of the second optical fiber system is to be $d_2$; and
the light emitting end of the first optical fiber system and the light receiving end of the second optical fiber system are provided in a region where a diameter is smaller than diameter $2d_1+d_2$ with the optical axis of the condenser lens system as a central axis.

3. The probe of claim 2, wherein,
a region a distance $d_2/2$ or more inward from an outer circumference of an inner region where the light emitting end of the first optical fiber system and the light receiving end of the second optical fiber system can be provided is to be a region $\alpha$;
a region with a diameter smaller than a diameter $d_1+d_2$ including as a central axis the central axis of the light emitting end of the first optical fiber system is to be a region $\beta$;
a region with a diameter smaller than the diameter $d_1+d_2$ including as a central axis an axis in a position symmetrical to the central axis of the light emitting end of the first optical fiber system with the optical axis of the condenser lens system as a center is to be a region $\gamma$; and
the central axis of the light receiving end of the second optical fiber system is positioned in a region within the region $\alpha$ not including the region $\beta$ and the region $\gamma$.

4. The probe of claim 3, wherein, a distance described below is a range from a same size to 1.4 times a focal length of the condenser lens, the distance between (i) the light emitting end of the first optical fiber system and the light receiving end of the second optical fiber system and (ii) a first surface of a lens which is included in the condenser lens system and which is closest to a second optical fiber system side, the first surface on a light receiving end side of the second optical fiber system.

5. The probe of claim 3, wherein, a ratio $r_1/r_2$ is within a range of −0.05 to 0.05 when a curvature radius of a first surface of the condenser lens is $r_1$ and a curvature radius of a second surface opposite of the first surface is $r_2$.

6. The probe of claim 2, wherein,
a diameter including as a central axis the optical axis of the condenser lens system in an inner region where the light emitting end of the first optical fiber system and the light receiving end of the second optical fiber system can be provided is to be a probe effective internal diameter D $(D<2d_1+d_2)$; and
the first optical fiber system, the second optical fiber system, and the condenser lens system are positioned so that a distance $d_3$ between an axis in a position symmetrical to the central axis of the light emitting end of the first optical fiber system with the optical axis of the condenser lens system as a center and the central axis of the light receiving end of the second optical fiber system satisfies a relation of $(d_1+d_2)/2<d_3<D-(d_1+d_2)/2$.

7. The probe of claim 1, wherein, the first optical fiber system and the second optical fiber system are positioned so that at least a portion of an outer circumference comes into contact with each other.

8. The probe of claim 7, wherein, at least one of the first and the second optical fiber systems includes a bundle of a plurality of optical fibers, and a portion of an outer circumference of the other optical fiber system is positioned within a circumscribed circle of the one optical fiber system including the bundle of plurality of optical fibers.

9. The probe of claim 7, wherein, at least one of the first and the second optical fiber systems includes a bundle of a plurality of optical fibers, and an outer circumference of the other optical fiber system is not positioned within a circumscribed circle of the one optical fiber system including the bundle of plurality of optical fibers.

10. The probe of claim 1, wherein, the first optical fiber system and the second optical fiber system are positioned separated from each other.

* * * * *